United States Patent [19]
Reznik

[11] Patent Number: 5,768,472
[45] Date of Patent: Jun. 16, 1998

[54] APPARATUS AND METHODS FOR RAPID ELECTROHEATING AND COOLING

[76] Inventor: David Reznik, 12690 Viscaino Rd., Los Altos Hills, Calif. 94022

[21] Appl. No.: 460,519

[22] Filed: Jun. 2, 1995

Related U.S. Application Data

[63] Continuation-in-part of Ser. No. 252,120, Jun. 1, 1994, Pat. No. 5,583,960.

[51] Int. Cl.⁶ .............................. H05B 3/03; H05B 6/54; A23L 3/00
[52] U.S. Cl. .......................... 392/321; 219/772; 99/358; 426/244; 392/314
[58] Field of Search ..................................... 392/320, 321, 392/319, 314; 219/771, 776, 772, 775; 99/358, DIG. 14; 426/244

[56] References Cited

U.S. PATENT DOCUMENTS

| | | |
|---|---|---|
| 535,267 | 3/1895 | Wagner et al. . |
| 684,746 | 10/1901 | Chapman . |
| 731,339 | 6/1903 | Chapman . |
| 1,147,558 | 7/1915 | Shelmerdine . |
| 1,360,447 | 11/1920 | Rudd . |
| 1,398,630 | 11/1921 | Dawe ........................... 392/320 |
| 1,431,580 | 10/1922 | Graetzer et al. . |
| 1,522,188 | 1/1925 | Hull . |
| 1,775,579 | 9/1930 | Woodrich . |
| 1,813,064 | 7/1931 | Matzka . |
| 1,934,703 | 11/1933 | Golden . |
| 2,081,243 | 5/1937 | Macy . |
| 2,438,582 | 3/1948 | Southerwick . |
| 2,472,708 | 6/1949 | Jones . |
| 2,473,041 | 6/1949 | Urbain et al. . |
| 2,495,415 | 1/1950 | Marshall . |
| 2,510,796 | 6/1950 | Brown . |
| 2,550,584 | 4/1951 | Mittelmann . |
| 2,564,579 | 8/1951 | Parmenter et al. . |
| 2,565,311 | 8/1951 | Koonz et al. . |

(List continued on next page.)

FOREIGN PATENT DOCUMENTS

| | | |
|---|---|---|
| 2100618 | 1/1994 | Canada . |
| 0 032 840 | 7/1981 | European Pat. Off. . |
| 0 457 179 | 11/1981 | European Pat. Off. . |
| 230-978-A | 1/1986 | European Pat. Off. . |
| 0 497 099 | 8/1992 | European Pat. Off. . |

(List continued on next page.)

OTHER PUBLICATIONS

Palaniappan, S., "Ohmic Heating of Foods: Studies on Microbicidal Effect of Electricity, Electrical Conductivity of Foods, and Heat Transfer In," PH.D. Thesis, The Ohio State University, 1991.

Palaniappan, S. et al., "Effects of Electricity on Microorganisms: A review, " Journal of Food Processing and Preservation vol. 14, No. 5 (Oct.,1990), pp. 383–414.

(List continued on next page.)

*Primary Examiner*—Philip H. Leung
*Attorney, Agent, or Firm*—Fish & Neave; Jeffrey H. Ingerman; Brett G. Alten

[57] ABSTRACT

Methods and apparatus for electroheating an electrically conducting flowable material are provided. In a preferred embodiment, flowable material is conveyed from an entrance passageway to first and second electrode assemblies. The flowable material is then conveyed from the first and second electrode assemblies to an exit passageway. Voltages of opposite polarity are respectively applied to the first and second electrode assemblies so that a first electric current passes through the flowable material as it is conveyed from the entrance passageway to the first and second electrode assemblies, and a second electric current passes through the flowable material as it is conveyed from the first and second electrode assemblies to the exit passageway, in order to electroheat the flowable material. The flowable material preferably is rapidly cooled after being electroheated. The present invention may, for example, advantageously be used to electroheat biological proteinaceous matter, such as liquid egg or milk.

103 Claims, 2 Drawing Sheets

U.S. PATENT DOCUMENTS

| | | |
|---|---|---|
| 2,582,281 | 1/1952 | Roberton . |
| 2,585,970 | 2/1952 | Shaw . |
| 2,685,833 | 8/1954 | Hagopian . |
| 2,799,216 | 7/1957 | Coulter . |
| 2,838,640 | 6/1958 | Mann et al. . |
| 3,315,681 | 4/1967 | Poppendiek . |
| 3,327,086 | 6/1967 | Cable . |
| 3,625,843 | 12/1971 | Doevenspeck . |
| 3,632,962 | 1/1972 | Cherniak . |
| 3,664,929 | 5/1972 | White et al. . |
| 3,709,802 | 1/1973 | Okuhara et al. . |
| 3,753,886 | 8/1973 | Myers . |
| 3,796,857 | 3/1974 | Henley et al. . |
| 3,855,531 | 12/1974 | Fielibert et al. . |
| 3,867,610 | 2/1975 | Quaintance . |
| 3,877,360 | 4/1975 | Vigerstrom . |
| 3,919,052 | 11/1975 | Fresnel et al. . |
| 3,949,099 | 4/1976 | Kaufman . |
| 4,091,119 | 5/1978 | Bach . |
| 4,109,566 | 8/1978 | Vigerstrom . |
| 4,177,719 | 12/1979 | Balaguer . |
| 4,211,887 | 7/1980 | Williamson .................................. 13/6 |
| 4,251,715 | 2/1981 | Petersson et al. . |
| 4,260,874 | 4/1981 | Will . |
| 4,369,351 | 1/1983 | Massey et al. ........................... 219/284 |
| 4,378,846 | 4/1983 | Brock . |
| 4,386,110 | 5/1983 | Komeyasu et al. . |
| 4,417,132 | 11/1983 | Simpson . |
| 4,420,382 | 12/1983 | Riedl . |
| 4,457,221 | 7/1984 | Geren . |
| 4,496,594 | 1/1985 | Miyahara . |
| 4,522,834 | 6/1985 | Miyahara . |
| 4,524,079 | 6/1985 | Hofmann . |
| 4,695,472 | 9/1987 | Dunn et al. . |
| 4,723,483 | 2/1988 | Papchenko et al. . |
| 4,739,140 | 4/1988 | Reznik . |
| 4,808,425 | 2/1989 | Swartzel st al. . |
| 4,838,154 | 6/1989 | Dunn et al. . |
| 4,853,238 | 8/1989 | Huang . |
| 4,857,343 | 8/1989 | Hekal . |
| 4,871,559 | 10/1989 | Dunn et al. . |
| 4,927,994 | 5/1990 | Leger . |
| 4,953,536 | 9/1990 | Israelsohn et al. . |
| 4,957,759 | 9/1990 | Swartzel et al. . |
| 4,957,760 | 9/1990 | Swartzel et al. . |
| 4,959,525 | 9/1990 | Stirling et al. . |
| 4,971,819 | 11/1990 | Miyahara . |
| 4,971,827 | 11/1990 | Huang . |
| 4,994,291 | 2/1991 | Swartzel et al. . |
| 5,019,407 | 5/1991 | Swartzel et al. . |
| 5,019,408 | 5/1991 | Swartzel et al. . |
| 5,048,404 | 9/1991 | Bushnell et al. . |
| 5,084,153 | 1/1992 | Mosse et al. . |
| 5,085,882 | 2/1992 | Rausing . |
| 5,091,152 | 2/1992 | Thomas, Sr. . |
| 5,105,724 | 4/1992 | Swartzel et al. . |
| 5,167,976 | 12/1992 | Papetti . |
| 5,226,106 | 7/1993 | Stirling . |
| 5,235,905 | 8/1993 | Bushnell et al. . |
| 5,266,338 | 11/1993 | Cascione et al. . |
| 5,288,471 | 2/1994 | Corner . |
| 5,290,583 | 3/1994 | Reznik et al. . |
| 5,326,530 | 7/1994 | Bridges . |
| 5,415,882 | 5/1995 | Knipper et al. ........................... 426/237 |
| 5,514,391 | 5/1996 | Bushnell et al. ........................... 426/237 |

FOREIGN PATENT DOCUMENTS

| | | |
|---|---|---|
| 0 685 987 | 12/1995 | European Pat. Off. . |
| 2513087 | 3/1983 | France . |
| 945 582 | 7/1956 | Germany . |
| 1 075 570 | 11/1957 | Germany . |
| 47-48542 | 6/1972 | Japan . |
| 24735 | 2/1931 | Netherlands . |
| 639158 | 12/1978 | U.S.S.R. . |
| 683034 | 3/1979 | U.S.S.R. . |
| 895141 | 5/1962 | United Kingdom . |
| 904371 | 8/1962 | United Kingdom . |
| 2068200 | 8/1981 | United Kingdom . |
| 2 147 776 | 5/1985 | United Kingdom . |
| 2 164 732 | 3/1986 | United Kingdom . |
| 2 282 052 | 3/1995 | United Kingdom . |
| WO 8900384 | 1/1989 | WIPO . |
| WO 9015547 | 12/1990 | WIPO . |
| WO 93/04421 | 3/1993 | WIPO . |
| WO 9319620 | 10/1993 | WIPO . |
| WO 94/11681 | 5/1994 | WIPO . |
| WO 94/18845 | 9/1994 | WIPO . |
| WO 95/10943 | 4/1995 | WIPO . |

OTHER PUBLICATIONS

Palaniappan, S. et al., "Experimental Studies on Electroconductive (Ohmic) Heating of Liquids," prepared for an American Society of Agricultural Engineers Meeting Presentation ( Dec. 12–15, 1989), Paper No. 89–6553.

Parrott, D.L. et al., "The Aseptic Processing of Fluids Containing Particulates from ⅛ " to 1" size, " prepared for presentation at American Institution of Chemical Engineers 1988 Summer Meeting (Aug. 21–24, 1988) (Unpublished), Paper No. 60e.

Reznik, D., "Electroheating," Dec. ,1989.

Sastry, S.K., "A Model for Heating of Liquid–Particle Mixtures in a Continuous Flow Ohmic Heater," Journal of Food Process Engineering 15 (1992), pp. 263–278.

Sastry, S.K. et al., "Mathematical Modeling and Experimental Studies on Ohmic Heating of Liquid–Particle Mixtures in a Static Heater," Journal of Food Process Engineering 15 (1992), pp. 241–261.

Sastry, S.K. et al., "Ohmic Heating of Liquid–Particle Mixtures," Food Technology (Dec., 1992), pp. 64–67.

Alkskog, L., "High Temperature pasteurization of Liquid Whole Egg," Process Technology, pp. 16–18.

Hamid–Samimi, M.H. et al., "Aseptic Packaging of Ultrapasteurized Egg, Design and Economic Considerations," publication date unknown, but a copy was transmitted to Mr. Merle Kirk under cover of a letter dated Aug. 21,1985 from Prof. Hersell Ball, Jr.

Hanson et al., "Pasteurization of Liquid Egg Products," Received for publication Nov. 16, 1946 pp. 277–283.

Madsen, M., "Pasteurization of Egg Products," Sundhedsplejen (Dec., 1958), 102–105 and translation thereof.

Murdock et al., "The Pasteurization of Liquid Whole Egg," issued from the Office of Medical Research Council, 38, Old Queen Street, Westminster, S.W.I.

Parrott, D.L., "Use of Ohmic Heating for Aseptic Processing of Food Particulates," Food Technology (Dec., 1992), pp. 68–72.

Russell, M.J., "Live Long and Prosper," Food Engineering, Dec., 1992, pp. 77–80.

Winter et al., "Pasteurization of Liquid Egg Products. I. Bacteria Reduction in Liquid Whole Egg and Improvement in Keeping Quality," Journal Paper No. J–1300 of the Town Agricultural Experimental Station, received from publication on Jun. 18,1945, 229–245.

Winter et al., "Pasteurization of Liquid Egg Products III. Destruction of Salmonella in Liquid Whole Egg," American Journal of Public Health, vol. 36, pp. 451–460 (1946).

"Annual Report of Cooperative Regional Projects" Supported by Allotment of the Regional Fund, Hatch Act, as Amended Aug. 11,1955, Jan. 1 to Dec. 31,1984, Raleigh, North Carolina. Approved by Chairman Hershell Ball, Jr. on March 14,1985.

Ball, H.R. Jr. et al., "Function and Shelf Life of Ultrapasteurized, Aseptically packaged Whole Egg" Abstract, Poultry Science Association Annual Meeting –Jul. 29 –Aug. 2,1985, Iowa State University, Ames.

Dinnage, D.F., "Continuous Aseptic Processing Using the Ohmic Heating Process," CHanging Food Technology 3, Food Technology: A view of the Future (Selected Papers from the Sixth Eastern Food Sciences & Technology Conference), Edited by Allen Freed (1990), pp. 29–41.

Essary, E.O. et al., "New Uses of Heated Aseptically Packaged Fluid Egg Products," Department of Food Science and Technology, and Chemical Engineering, Virginia Polytechnic Institute and State University, Blacksburg, VA 1983.

Hamid–Samini, M.H., "Criteria Development for Extended Shelf–Life Pasteurized Liquid Whole Egg," Ph.D. Thesis, North Carolina State University, Raleigh, North Carolina, 1984.

Jacobs, L.C., "Aseptic packaging promises a new role for pasteurized liquid eggs," Apr. ,1981.

Sill, M., "NCSU researchers crack the secret of long shelflife for eggs," The News and Observer, Raleigh, North Carolina, Sep. 3, 1985.

Stone, W.K. et al., "Aseptic Processing of Liquid Eggs Pasteurized in a Teflon Heat Exchanger," 1983.

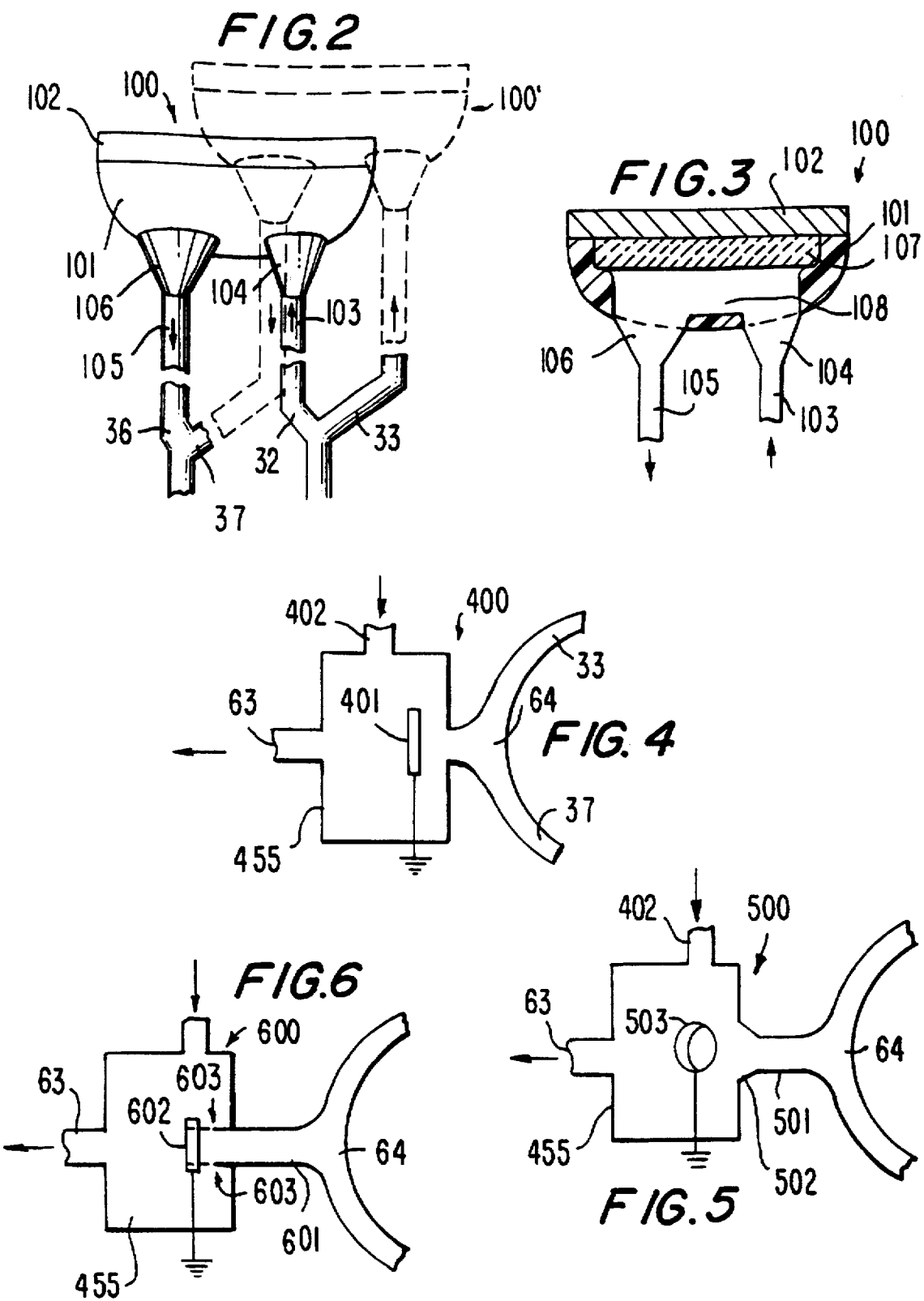

5,768,472

1

APPARATUS AND METHODS FOR RAPID ELECTROHEATING AND COOLING

CROSS REFERENCE TO RELATED APPLICATION

This application is a continuation-in-part of U.S. patent application Ser. No. 08/252,120, filed Jun. 1, 1994, now U.S. Pat. No. 5,583,960.

BACKGROUND OF THE INVENTION

The present invention relates to methods and apparatus for electroheating flowable materials such as liquid foods and biological products by passage of electrical current therethrough. The present invention is particularly well-suited for rapidly heating liquid foods such as liquid egg and milk, as well as media used in the biochemical and pharmaceutical industries.

Copending U.S. patent application Ser. No. 08/252,120 U.S. Pat. No. 5,583,960 relates to methods and apparatus for electroheating flowable materials. The apparatus described therein comprises a relatively narrow nonconducting tube in which each end of the tube is coupled to a separate electrode having a relatively large surface area. A voltage is applied across the electrodes so that a current flows between the large-surface-area electrodes via the relatively narrow tube. Because the surface area of the electrodes is relatively large, the current density is relatively low near the electrodes and very little heating occurs. However, because the tube is relatively narrow, the current density is relatively large in the tube and rapid heating occurs. Such an apparatus is advantageous because only a relatively low current density flows through the material near the electrode surfaces, which is believed to prevent, or at least reduce, arcing and fouling of the apparatus. In the case of electroheating foods, such an apparatus is also believed to reduce detrimental coagulation of the food.

Each electrode preferably is coupled to the narrow tube by a spherical conical structure. The flowable material flows into (or out of) the conical structure, preferably through holes in the electrode, and is then funneled into (or out of) the narrow tube.

A potential drawback of the previous apparatus is that the flowable material may dwell in the conical structure for a relatively long period of time—i.e., the flowable material may remain within the conical structure for a relatively long time before exiting the conical structure—even though it has exited the heating zone of the narrow tube. This may be troublesome for certain flowable materials such as food products. When certain foods are electroheated, it is important that the food does not remain at a relatively high temperature for an extended period of time. For example, when liquid egg is heated to relatively high temperatures (e.g., 180° F. (82° C.)) it may coagulate if it is not rapidly cooled. Thus, if liquid egg were heated to a relatively high temperature while passing through the narrow tube of a previous apparatus, the liquid egg may then coagulate while it is within the spherical conical structure.

One solution to this drawback would be to decrease the size of the conical structure and the electrode. Although this may decrease the dwell time within the conical structure, the increased current density at the electrode surface (due to the decreased surface area) may cause arcing and fouling of the apparatus. In the case of electroheating liquid egg, the increased current density may cause the liquid egg to coagulate on the electrode surfaces.

In view of the foregoing it would be desirable to provide methods and apparatus for rapidly electroheating flowable material without having a relatively long dwell time at high temperatures.

2

It would also be desirable to rapidly cool the flowable material soon after it has been electroheated.

SUMMARY OF THE INVENTION

It is therefore an object of the present invention to provide methods and apparatus for rapidly electroheating flowable material without having a relatively long dwell time at high temperatures.

It is also an object of the present invention to rapidly cool the flowable material soon after it has been electroheated.

These and other objects of the present invention preferably are accomplished in accordance with the principles of the invention by providing the following. First and second electrode assemblies are provided. An inflow assembly is provided having an entrance passageway and first and second inflow passageways which communicate with the entrance passageway. The first inflow passageway is coupled to the first electrode assembly so that a first portion of the flowable material flows from the entrance passageway to the first electrode assembly. The second inflow passageway is coupled to the second electrode assembly so that a second portion of the flowable material flows from the entrance passageway to the second electrode assembly. An outflow assembly is provided having an exit passageway and first and second outflow passageways which communicate with the exit passageway. The first outflow passageway is coupled to the first electrode assembly so that the first portion of the flowable material flows from the first electrode assembly to the exit passageway. The second outflow passageway is coupled to the second electrode assembly so that the second portion of the flowable material flows from the second electrode assembly to the exit passageway. Each of the first and second electrode assemblies preferably comprises at least one electrode which is in electrical contact with the flowable material. Voltages of opposite polarity preferably are respectively applied to the first and second electrode assemblies so that a first electric current passes through the first and second inflow passageways and a second electric current passes through the first and second outflow passageways, in order to electroheat the flowable material.

In a preferred embodiment, the first and second inflow passageways have respective first and second inflow passageway lengths which are substantially equal. The entrance passageway preferably is coupled to the first and second inflow passageways so that it is substantially half-way between the first and second electrode assemblies. The first and second outflow passageways have respective first and second outflow passageway lengths which preferably are substantially equal. The exit passageway preferably is coupled to the first and second outflow passageways so that it is substantially half-way between the first and second electrode assemblies.

In another preferred embodiment, the at least one electrode of each the first and second electrode assemblies has a surface area which is relatively large as compared to respective first and second diameters of the first and second inflow passageways, and which is relatively large as compared to respective first and second diameters of the first and second outflow passageways.

In yet another preferred embodiment, a cooling device is disposed in the exit passageway for rapidly cooling the flowable material after it has been electroheated.

The following method preferably is used to electroheat flowable material in accordance with the present invention. First, flowable material is provided. A first portion of the flowable material is conveyed from an entrance passageway to a first electrode assembly. A second portion of the flowable material is conveyed from the entrance passageway to a second electrode assembly. The first portion of the flowable material is then conveyed from the first electrode assembly to an exit passageway. The second portion of the flowable material is then conveyed from the second electrode assembly to the exit passageway. Voltages of opposite polarity are applied to the first and second electrode assemblies so that a first current flows through the first and second portions of the flowable material as they are respectively conveyed from the entrance passageway to the first and second electrode assemblies, and so that a second current flows through the first and second portions of the flowable material as they are respectively conveyed from the first and second electrode assemblies to the exit passageway, in order to electroheat the first and second portions of the flowable material.

In a preferred embodiment, the flowable material is rapidly cooled after being electroheated.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 2 is an elevational view of an electrode assembly which may preferably be used with the apparatus of FIG. 1;

FIG. 3 is a cross-sectional view of the electrode assembly of FIG. 2;

FIG. 4 is a partial schematic view of a further preferred embodiment of the present invention;

FIG. 5 is a partial schematic view of a first variation of the embodiment of FIG. 4; and FIG. 6 is a partial schematic view of a second variation of the embodiment of FIG. 4.

DETAILED DESCRIPTION OF THE INVENTION

Figure 1:
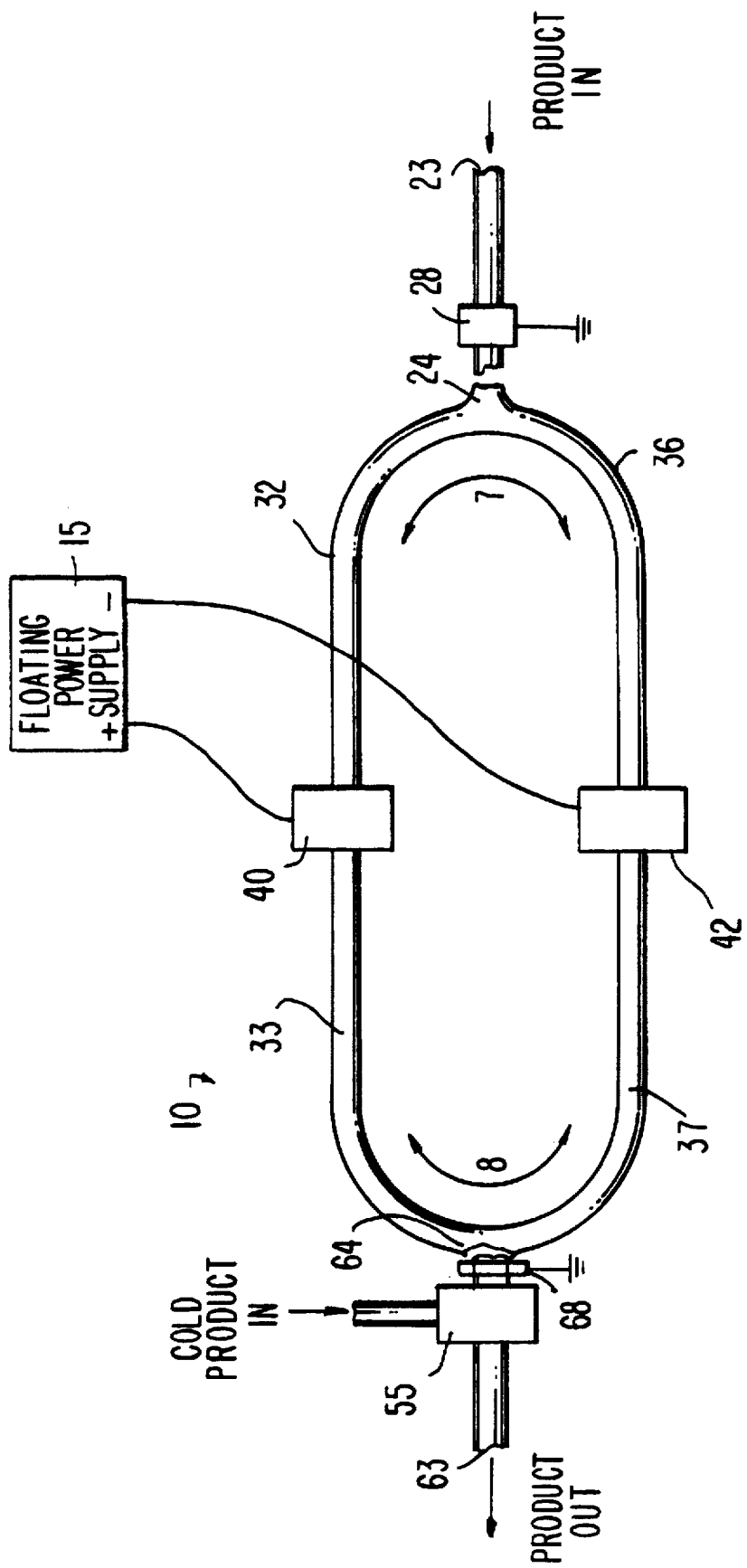
FIG. 1 is a simplified schematic diagram of an apparatus for electroheating flowable material constructed in accordance with the present invention.

The present invention is able to rapidly heat a flowable material and then rapidly cool the material. The present invention may, for example, be used advantageously to electroheat foods such as liquid egg and milk. In a preferred embodiment of the present invention, flowable material is conveyed from an entrance passageway to first and second electrode assemblies. The flowable material is then conveyed from the first and second electrode assemblies to an exit passageway. Voltages of opposite polarity are applied to the first and second electrode assemblies so that a first electric current passes through the flowable material as it is conveyed to the electrode assemblies, and a second electric current passes through the flowable material as it is conveyed away from the electrode assemblies. The first and second currents heat the flowable material. The flowable material preferably is rapidly cooled after being heated.

Each of the electrode assemblies has at least one electrode which is in electrical contact with the flowable material. The surface area of the electrodes preferably is relatively large as compared to the diameters of the conduits through which the flowable material flows.

A preferred embodiment of the present invention is shown in FIG. 1. Device 10 may be used to electroheat any electrically-conducting flowable material including liquid egg, milk, soups, sauces, biological products such as blood and media for fermentation and cell culture, and numerous other materials. Device 10 may, for example, advantageously be used to pasteurize liquid egg, or to sterilize liquid egg in order to provide shelf-stable liquid egg. Device 10 may also advantageously be used to pasteurize milk, or to sterilize milk in order to provide shelf-stable milk.

Flowable material enters the device through entrance or inlet 23 and then flows into conduits 32 and 36 via junction 24. Substantially equal portions of flowable material preferably pass into each of conduits 32 and 36. The flowable material in conduit passes through first electrode assembly 40 and then conduit 33, while the flowable material in conduit 36 passes through second electrode assembly 42 and then conduit 37. The material from both conduits is then recombined at junction 64, and then preferably passes through mixing chamber 55 before exiting the device through exit or outlet 63. Mixing chamber 55 preferably is provided in order to cool the electroheated flowable material.

In a preferred embodiment, conduits 32 and 36 are formed from a single curved tube. The two ends of the tube are coupled to the electrode assemblies 40, 42 and junction 24 may be formed by providing a hole in the tube to which inlet tube 23 may be connected. In this way, the portion of the single curved tube between junction 24 and electrode assembly 40 forms conduit 32, while the portion of the single curved tube between junction 24 and electrode assembly 42 forms conduit 36. Conduits 33 and 37 may preferably be constructed in a similar manner.

In another preferred embodiment (not shown), conduits 32 and 36 are separate tubes. A Y-shaped connector preferably is provided to serve as junction 24, in order to allow flowable material to pass from inlet 23 to conduits 32 and 36. Conduits 33 and 37 may preferably be constructed in a similar manner.

In either of these embodiments, the tubes should be able to withstand the high pressures developed in the relatively narrow diameter tubes by the fast-flowing material to be heated.

Floating power supply 15 (e.g., a floating transformer) is electrically coupled to electrode assemblies 40 and 42. The voltage outputs provided by the floating power supply are such that, with respect to ground, each electrode assembly preferably is at a voltage of substantially equal magnitude, but opposite polarity, as the other electrode assembly. For purposes of illustration only, the following example is given in which the applied AC voltage ranges from −2000 Volts to +2000 Volts (i.e., 4000 Volts peak-to-peak). The voltage applied to electrode assembly 42 is +2000 volts at the beginning of the alternating cycle, and decreases with time, while the voltage applied to electrode assembly 40 preferably is −2000 Volts and increases with time (i.e., becomes less negative and eventually positive).

Floating power supply 15 preferably provides an alternating electric current having a frequency of up to about 100 kHz or more, preferably about 10 kHz, and more preferably between about 50 Hz and about 60 Hz, which is available from a common household-type power outlet. At the higher frequencies, electrolytic phenomena are substantially eliminated. The same is substantially true at about 10 kHz if the electrodes are made of graphite as is preferred according to the present invention. While some hydrogen formation and some reduction occur at 50 Hz or at 60 Hz, the small amount of reduction when graphite electrodes are used may be beneficial. Any such effects are minimized, in any event, by the low currents used in the system according to the invention.

An electric current flows between the electrode assemblies along two separate paths 7 and 8. The current flowing along path 7 passes through conduits 32 and 36, while the current along path 8 passes through conduits 33 and 37.

While in the embodiment shown there is one first fluid flow path 32–33 and one second fluid flow path 36–37, resulting in one first current flow path 7 and one second current flow path 8, there can also be multiple paths connected to a multi-phase power source (not shown). For example, there could be three first fluid flow paths 32–33 and three second fluid flow paths 36–37, each having its own electrode, in which case power supply 15 would be a three-phase supply.

Conduits 32 and 36 preferably are substantially equal in length so that junction 24 is substantially halfway between the electrode assemblies 40 and 42. Conduits 32 and 36 also preferably have substantially equal diameters. Thus, the electrical resistance of the flowable material within conduit 36 is substantially equal to the resistance of the flowable material within conduit 32. Because of this and the fact that a voltage of equal magnitude, but opposite polarity, preferably is applied to the electrode assemblies 40 and 42, the voltage at junction 24 is substantially zero. Since the voltage at junction 24 is substantially zero, only a small amount of current, if any, flows "upstream" beyond junction 24. A grounded collar 28 (i.e., a collar connected to an electrical ground), which is in electrical contact with the flowable material, preferably is provided upstream of junction 24 in order to ensure that current does not flow upstream past the grounded collar (i.e., so that current does not flow into inlet 23). Preferably, collar 28 is at a distance from junction 24 at least as great as the length of each conduit 32, 36, so that the resistance of the material in inlet tube 23 is at least as great as that of the material in tubes 32, 36, further insuring against current flow upstream. Further, the diameter of the tube between junction 24 and collar 28 may be reduced as compared to that of tubes 32, 36, still further increasing the resistance of the material in the inlet tube and further insuring against current flow. Grounded collar 28, which is preferably made of graphite, thus increases the safety of the apparatus.

The substantially equal electrical currents flowing through the material within conduits 32 and 36 heat the material in the respective conduits by substantially the same amount. Thus, the flowable material arriving at electrode assembly 40 preferably is at substantially the same temperature as the material arriving at assembly 42.

The flowable material is similarly electroheated as it passes through the respective conduits 33 and 37. The lengths of conduits 33 and 37 preferably also are substantially equal and preferably have substantially equal diameters so that the resistances of the two conduits are substantially equal. For reasons similar to those given above with respect to junction 24, the voltage at junction 64 is substantially zero. A grounded collar 68 preferably is provided near junction 64 in order to prevent electric current from flowing "downstream" past outlet 63. The distance from junction 64 to outlet 63, as well as the dimensions of the outlet tube, are governed by considerations similar to those governing collar 28 and inlet 23, although here holding time should be selected to prevent detrimental effects on heat-sensitive flowable materials.

The material in conduit 33 preferably is heated by substantially the same amount as the material in conduit 37. Thus, the material from each conduit is substantially equal in temperature at junction 64.

In accordance with the present invention, conduits 33 and 37 may be of a greater or lesser length than conduits 32 and 36, and conduits 33 and 37 may have a greater or lesser diameter than conduits 32 and 36. The lengths and diameters of the entry leg (i.e., conduits 32 and 36) and exit leg (i.e., conduits 33 and 37) may be designed to provide unequal amounts of heating in the entry and exit legs. For example, the diameter of the entry leg may be reduced relative to the exit leg, thereby increasing the resistance of the entry leg and thus decreasing the amount of heating which occurs in the entry leg (heating is inversely proportional to the resistance of the leg). Those skilled in the art will appreciate that the lengths and diameters of the legs may be designed to provide the proper amount of heating in the respective legs for the particular flowable material under treatment. For certain materials, it is advantageous to adjust the resistance of the exit leg relative to the entry leg so as to provide for very rapid heating of the material in the exit leg, to reduce the dwell time at the higher temperatures. This may be accomplished by adjusting the resistance of the exit leg so that it is less than the resistance of the entry leg. After being rapidly heated, the material may then preferably be rapidly cooled. An example of the use of the present invention to rapidly electroheat liquid egg is given below.

In a preferred embodiment, the flowable material flows into mixer 55 after being recombined at junction 64. The length and diameter of the conduit between junction 64 and mixer 55 may be selected in order to provide any desired holding time of the flowable material at an elevated temperature. In mixer 55, the heated flowable material preferably is mixed with a stream of relatively cold flowable material in order to rapidly cool the heated material. The stream of relatively cold material preferably is the same type of material as the electroheated material, and preferably has already been treated (preferably by electroheating as described herein) in order to prevent contamination of the electroheated material. The mixer may preferably be a "Y-shaped" mixing chamber as described in U.S. Pat. No. 5,290,583 of Reznik and Knipper, which is hereby incorporated by reference herein. Such a device has two inlet conduits and an outlet conduit. Relatively hot material enters a mixing chamber through one inlet, while relatively cold material enters the chamber through the other inlet. After being mixed together, the material exits through the outlet. Such a mixer is able to rapidly cool heated flowable material.

Other types of cooling devices may be used instead of mixer 55 in order to cool the heated flowable material. A conventional plate heat exchanger may, for example, be used to cool the flowable material. In general, any type of cooling device may be used as long as it is able to rapidly cool the flowable material.

After being cooled, the flowable material exits the device through outlet 63. The flowable material may then be further cooled by conventional cooling means. The flowable material may, for example, be cooled by conventional means to a temperature of about 40° F. (about 4° C.).

It is preferable to provide a back pressure valve at outlet 63 in order to maintain a minimum pressure of the flowable material within the device. If pressure within the device is not maintained, arcing and fouling of the device may occur.

The present invention provides the advantage that the heated material passing through junction 64 does not dwell for a relatively long period of time within an electrode assembly. In fact, the flowable material may preferably be rapidly cooled after passing through junction 64. This is particularly important for certain foods such as liquid egg which may coagulate if held at an elevated temperature for a period of time.

It will be clear to those skilled in the art that the flowable material may be heated in further heating stages (which may or may not be electroheating stages) after being recombined at junction 64.

The conduits and electrode assemblies of electroheating device 10 preferably are constructed in accordance with the principles set forth in the aforementioned U.S. patent application Ser. No. 08/252,120, which is hereby incorporated by reference herein. The conduits therefore preferably are relatively narrow, while the electrode assemblies have relatively large surface areas. However, other types of electrode assemblies may be used in accordance with the present invention, including electrode assemblies which do not have relatively large surface areas.

Although shown schematically in FIG. 1 as lying in a single plane, with the flowable material flowing substantially in a single direction from entry to exit, apparatus 10 according to the present invention is preferably so that the flowable material to be heated flows in a first direction toward electrodes 40, 42 in entry leg conduits 32, 33, and in a second direction substantially parallel to but opposite the first direction away from electrodes 40, 42 in exit leg conduits 36, 37. The flow of material thus doubles back on itself (see FIG. 2) so that outlet 63 is near inlet 23.

An example of an electrode assembly 100 which may preferably be used as electrode assembly 40 in apparatus 10 is illustrated in FIGS. 2 and 3. A second assembly 100' which is a mirror image of assembly 100 can be used as electrode assembly 42, and is shown in phantom. Electrode assembly 100 comprises an electrically insulating housing 101 (e.g., of a plastic material such as ULTEM® 1000 resin available from the General Electric Company, of Fairfield, Conn.). An inlet tube 103 (which is an extension of first conduit 32, 33) enters a first conical chamber 104, and an outlet tube 105 (which is an extension of second conduit 36, 37) exits a second conical chamber 106, which preferably has a greater volume than first conical chamber 104. An electrode plate 107, preferably of graphite, is located within housing 101. Plate 107 is in intimate electrical contact with a conductive plate 102 (preferably of stainless steel), which closes off housing 101 and is electrically connected (not shown) to floating power supply 15. Plate 107 thus is energized and serves as electrode 40 or 42.

Flowable material being heated enters through inlet tube 103 into first conical chamber 104, and flows through channel or plenum 108, in which it is in contact with graphite electrode plate 107, and into second conical chamber 106, whence it exits through outlet tube 104.

Material entering inlet tube 103 is at the end of the first heating leg. In order to decrease the current density between the material and electrode plate 107, conical chamber 104 is provided. Similarly, conical chamber 106 is provided to decrease the current density between electrode plate 107 and material entering the second heating leg. Chamber 106 preferably is larger than chamber 104 because in the preferred embodiment, as described below, the apparatus is configured so that the current in the second leg is higher than that in the first leg. In order to keep the current density at acceptable levels at the electrode, then, chamber 106 is made larger than chamber 104.

Although electrode plate 107 preferably is made of a carbonaceous material such as pyrolytic treated graphite, it may be made of stainless steel. A description of other materials which may preferably, although not exclusively, be used with the present invention is given in the aforementioned U.S. patent application Ser. No. 08/252,120.

Referring to FIG. 1, an example of the use of the present invention to electroheat liquid egg is now given. In a preferred embodiment of the present invention for use to electroheat liquid egg to relatively high temperatures, conduits 32 and 36 preferably are longer than conduits 33 and 37, and conduits 32 and 36 preferably have a smaller diameter than conduits 33 and 37. The respective length and diameters of the entry and exit legs may be adjusted so that the resistance of the entry leg is approximately four times larger than that of the exit leg. For example, in order to heat about 500 pounds per hour of a proteinaceous material such as liquid egg, the diameter of conduits 32 and 36 (the entry leg) may be approximately 0.125 inch and the length of each conduit 32, 36 may be approximately 6 inches, and the diameter of conduits 33 and 37 (the exit leg) may be approximately 0.14 inch and the length of each conduit 33, 37 may be approximately 1.26 inches. This gives a resistance along path 7 of approximately 16,000Ω and a resistance along path 8 of approximately 4,000Ω. This allows more than twice as much current to flow in path 8 as compared to path 7, and thus more than two-thirds of the heating occurs in path 8, so that the liquid egg is rapidly heated to a relatively high temperature in the exit leg (path 8).

In a preferred embodiment, the liquid egg is heated from about 120° F. (about 49° C.) to about 150° F. (about 66° C.) as it passes through the entry leg, and then heated from about 150° F. (about 66° C.) to about 280° F. (about 138° C.) as it passes through the exit leg. After being heated to about 280° F. (about 138° C.), the liquid egg is then preferably rapidly cooled in mixing chamber 55 before it begins to coagulate. The liquid egg is preferably cooled to a temperature of about 160° F. (about 71° C.) in the mixing chamber.

The liquid egg is preferably heated in the exit leg for a very short period of time (e.g., less than one-tenth of a second (0.1 second), preferably less than about 0.02 second, and more preferably between about 0.005 second and about 0.05 second). In an apparatus having the dimensions given above and a flow rate of about 500 pounds of liquid egg per hour (i.e., 250 pounds per hour in each of conduits 33 and 37), at an applied voltage of about 10,000 volts the temperature of the liquid egg is raised from about 150° F. (about 66° C.) to about 280° F. (about 138° C.) in about 0.02 second in the exit leg. The present invention is thus able to provide a heating rate of about 6500° F. (about 3611° C.) per second.

Since the liquid egg preferably is heated in 0.02 second (or less), it is important that the liquid egg flows through the device at substantially constant velocity and pressure. If, for example, the flow of liquid egg paused for 0.02 second within the device, the amount of heat imparted to the liquid egg would about double, which may cause undesirable boiling or coagulation, which may lead to arcing. It is thus preferable to use a pump (not shown) which is able to provide an uninterrupted flow of liquid egg (or other flowable material) through the device at substantially constant pressure and velocity.

Although as stated above, the flowable material is cooled relatively quickly in mixer 55 after passing junction 64, there is still a period of "holding time"—after the material passes ground collar 68 and is no longer being heated—during which the material remains at an elevated temperature, until it can reach mixer 55. FIG. 4 shows an alternative embodiment in which there is little or no holding time between the cessation of heating and the cooling of the material.

The portions of the embodiment 400 of FIG. 4 that are not shown are substantially similar to the embodiment of FIG. 1. Only the portion of embodiment 400 adjacent junction 64 is shown. In embodiment 400, ground collar 68 is eliminated, and mixer 55 is replaced with receiving chamber 455 into which the flowable material flows directly from junction 64. The function of ground collar 68 is performed by suspended ground electrode 401 suspended in chamber 455. Electrode 401 preferably is a graphite disk and is spaced far enough from junction 64 to avoid affecting the flow of material into chamber 455. The disk may or may not be perforated to allow material to flow through it. Cooled flowable material, preferably recirculated from downstream of outlet 63, enters through conduit 402 to cool the flowable material more rapidly. Thus, in apparatus 400, there is substantially no holding time between the cessation of heating and the beginning of cooling.

If some holding time is desired, then, as shown in FIG. 5, a short section of conduit 501 (not shown to scale) can be provided between junction 64 and chamber 455. The length and diameter of conduit 501 can be adjusted to provide the desired holding time. The holding time is further determined by optional conical section 502, which, if provided, slows the flow of material in conduit 501. The length and diameter of conduit 501, as well as the dimensions of conical section 502, also should be chosen to provide the desired resistance. If no substantial additional heating is to occur, the resistance must decrease relative to conduits 33, 37, whether it is accomplished by decreasing the length of conduit 501 or increasing its diameter. Electrode 503 of apparatus 500 is preferably a hollow graphite hemisphere, instead of a disk as in apparatus 400, with its concave open side facing conduit 501 (to avoid presenting its convex face to the flow of current, which might cause the current to concentrate at a single point nearest conduit 501).

Alternatively, as shown in FIG. 6, a tube 601 extending into chamber 455 can be used to provide holding time, with (not shown) or without a conical section like conical section 502. As in the case of conduit 501, tube 601 (which is not shown to scale) is dimensioned to provide a desired resistance and holding time. In this embodiment, "suspended" electrode 602 is fixed to tube 601, which has a series of exit openings 603 about its periphery adjacent electrode 602.

Moreover, while suspended electrodes 401, 503 are provided mainly for safety (insofar as the voltage at junction 64 is substantially at ground as long as the resistance of the material in each of conduits 36, 37 is substantially the same), such suspended electrodes also can be used in linear electroheating systems, such as that described in the aforementioned application Ser. No. 08/252,120, where the ground electrode forms part of the heating circuit. Receiving chamber 455 may also be used in such a system for cooling. As shown in FIG. 6, in either a system such as that of FIG. 1, or a linear system as in said aforementioned application, ground electrode 602 can be fixed to the end of tube 602, with the flowable material exiting through a series of apertures 603 spaced about the periphery of tube 601, rather than through a perforated electrode as in said aforementioned application.

The present invention may preferably be used in order to provide shelf-stable (i.e., sterile) liquid egg. By rapidly heating and then cooling the liquid egg, the present invention is able to provide shelf-stable liquid egg without significant coagulation of the liquid egg.

In another embodiment, the present invention may preferably be used to rapidly heat milk in order to provide shelf-stable (i.e., sterile) milk. For example, milk may be heated from about 40° F. (about 4° C.) to about 160° F. (about 71° C.) in the entry leg, and then heated from about 160° F. (about 71° C.) to about 280° F. (about 138° C.) in the exit leg. In this example the lengths and diameters of conduits 32 and 36 are the same as those of conduits 33 and 37, so that the amount of heating in the entry leg is the same as in the exit leg. The lengths and diameters of the conduits and the flow rate of the milk are preferably chosen so that the milk travels through the exit leg (e.g. from electrode 40 to junction 64) in about 0.015 second, and more preferably in about 0.005 second. If the milk is thus heated from about 160° F. (about 71° C.) to about 280° F. (about 138° C.) in about 0.015 second, that represents a heating rate of about 8000° F. (about 4444° C.) per second. After being heated to about 280° F. (about 138° C.), the milk is held for an adequate holding time and then preferably is rapidly cooled in mixer 55. Milk treated in accordance with the present invention is shelfstable.

The shelf-stable milk produced in accordance with the present invention does not suffer from detrimental changes in flavor. Consumers of previous sterile milk products often report that the milk has an unpleasant "cooked" flavor. It is believed that sterile milk produced in accordance with the present invention does not suffer from detrimental changes in flavor for at least three reasons. First, sterile milk produced in accordance with the present invention is heated very rapidly and then quickly cooled. It is believed that minimizing the amount of time the milk is held at an elevated temperature minimizes degradation of the flavor of the treated milk. In the example given above, the milk is heated from about 160° F. (about 71° C.) to about 280° F. (about 138° C.) in only about 0.015 second or less. Such rapid heating followed by rapid cooling is believed to sterilize the milk while preserving the natural flavor of the milk.

The above examples are for illustrative purposes. Different temperature ranges and conduit sizes can be used in accordance with the present invention, and, in general, these will depend on the particular material which is being electroheated.

Thus, methods of and apparatus for electroheating flowable material have been described. Those skilled in the art will appreciate that various modifications can be made to the above description without departing from the spirit of scope of the invention, and that this invention is limited only by the claims which follow.

What is claimed is:

1. Apparatus for electroheating a flowable material comprising:

first and second electrode assemblies;

a dielectric inflow assembly having an entrance passageway and first and second inflow passageways which communicate with said entrance passageway, each of said inflow passageways having a diameter and a cross-sectional area, said first inflow passageway coupled to said first electrode assembly for allowing a first portion of said flowable material to flow from said entrance passageway to said first electrode assembly, said second inflow passageway coupled to said second electrode assembly for allowing a second portion of said flowable material to flow from said entrance passageway to said second electrode assembly; and a dielectric outflow assembly having an exit passageway and first and second outflow passageways which communicate with said exit passageway, each of said outflow passageways having a diameter and a cross-sectional area, said first outflow passageway coupled to said first electrode assembly for allowing said first portion of said flowable material to flow from said first electrode assembly to said exit passageway, said second outflow passageway coupled to said second electrode assembly for allowing said second portion of said flowable material to flow from said second electrode assembly to said exit passageway, wherein:

each of said first and second electrode assemblies comprises at least one electrode which is in electrical contact with said flowable material, said at least one electrode having a surface area that is relatively large compared to said cross-sectional areas of said inflow and outflow passageways so that the current density in the flowable material is relatively low near said at least one electrode, said flowable material having an electrical resistance inside every inflow passageway that is substantially equal, and wherein voltages of opposite polarity are respectively applied to said first and second electrode assemblies so that a first electric current passes through said first and second inflow passageways and a second electric current passes through said first and second outflow passageways, in order to electroheat said flowable material.

2. The apparatus of claim 1 wherein:
said first and second inflow passageways have respective first and second inflow passageway lengths which are substantially equal; and
said first and second outflow passageways have respective first and second outflow passageway lengths which are substantially equal.

3. The apparatus of claim 2 wherein said first and second outflow passageway lengths are substantially equal to said first and second inflow passageway lengths.

4. The apparatus of claim 2 wherein said first and second outflow passageway lengths are greater than said first and second inflow passageway lengths.

5. The apparatus of claim 2 wherein said first and second outflow passageway lengths are less than said first and second inflow passageway lengths.

6. The apparatus of claim 1 wherein said first and second inflow passageways have respective first and second inflow passageway diameters which are substantially equal, and wherein said first and second outflow passageways have respective first and second outflow passageway diameters which are substantially equal.

7. The apparatus of claim 6 wherein said first and second inflow passageway diameters are substantially equal to said first and second outflow passageway diameters.

8. The apparatus of claim 6 wherein said first and second inflow passageway diameters are greater than said first and second outflow passageway diameters.

9. The apparatus of claim 6 wherein said first and second inflow passageway diameters are less than said first and second outflow passageway diameters.

10. The apparatus of claim 1 further comprising:
a cooling device disposed in said exit passageway for rapidly cooling said flowable material after it has been electroheated.

11. The apparatus of claim 10 wherein said cooling device comprises:
a mixing chamber;
a first conduit for allowing said flowable material to enter said mixing chamber;
a second conduit for allowing relatively cold flowable material to enter said mixing chamber and mix with said flowable material in order to form cooled flowable material; and
a third conduit for allowing said cooled flowable material to exit said mixing chamber.

12. The apparatus of claim 11 wherein said cooling device further comprises a ground electrode suspended in said mixing chamber substantially adjacent said first conduit.

13. The apparatus of claim 12 wherein said ground electrode comprises graphite.

14. The apparatus of claim 12 wherein said ground electrode has a substantially circular cross section.

15. The apparatus of claim 14 wherein said ground electrode is a disk.

16. The apparatus of claim 14 wherein said ground electrode is a hollow partial sphere having a concave face facing said first conduit.

17. The apparatus of claim 1 further comprising an electrode at said entrance passageway which is coupled to an electrical ground.

18. The apparatus of claim 1 further comprising an electrode at said exit passageway which is coupled to an electrical ground.

19. The apparatus of claim 1 wherein voltages of substantially equal magnitude and opposite polarity are respectively applied to said first and second electrode assemblies.

20. The apparatus of claim 19 wherein said voltages are alternating voltages having a frequency up to about at least 100 kHz.

21. The apparatus of claim 20 wherein said frequency is about 10 kHz.

22. The apparatus of claim 20 wherein said frequency is between about 50 Hz and about 60 Hz.

23. The apparatus of claim 1 wherein said voltages are supplied by a floating power supply.

24. The apparatus of claim 1 wherein said first current is substantially equal in magnitude to said second current.

25. The apparatus of claim 1 wherein said first current is larger in magnitude than said second current.

26. The apparatus of claim 1 wherein said first current is smaller in magnitude than said second current.

27. The apparatus of claim 1 wherein:
said first and second inflow passageways comprise an inflow conduit having a first end coupled to said first electrode assembly and a second end coupled to said second electrode assembly, said inflow conduit having an inflow opening coupled to said entrance passageway for allowing said first portion of said flowable material to flow from said entrance passageway to said first electrode assembly and for allowing said second portion of said flowable material to flow from said entrance passageway to said second electrode assembly; and
said first and second outflow passageways comprise an outflow conduit having a first end coupled to said first electrode assembly and a second end coupled to said second electrode assembly, said outflow conduit having an outflow opening coupled to said exit passageway for allowing said first portion of said flowable material to flow from said first electrode assembly to said exit passageway and for allowing said second portion of said flowable material to flow from said second electrode assembly to said exit passageway.

28. The apparatus of claim 27 wherein:
said inflow opening is located at a position along said inflow conduit which is substantially half-way between said first and second electrode assemblies; and said outflow opening is located at a position along said outflow conduit which is substantially half-way between said first and second electrode assemblies.

29. The apparatus of claim 1 further comprising:
a cooling device disposed in said exit passageway for rapidly cooling said flowable material after it has been electroheated.

30. The apparatus of claim 29 wherein said cooling device comprises:
a mixing chamber;
a first conduit for allowing said flowable material to enter said mixing chamber;
a second conduit for allowing relatively cold flowable material to enter said mixing chamber and mix with said flowable material in order to form cooled flowable material; and
a third conduit for allowing said cooled flowable material to exit said mixing chamber.

31. The apparatus of claim 30 wherein said cooling device further comprises a ground electrode suspended in said mixing chamber substantially adjacent said first conduit.

32. The apparatus of claim 31 wherein said ground electrode comprises graphite.

33. The apparatus of claim 31 wherein said ground electrode has a substantially circular cross section.

34. The apparatus of claim 33 wherein said ground electrode is a disk.

35. The apparatus of claim 33 wherein said ground electrode is a hollow partial sphere having a concave face facing said first conduit.

36. The apparatus of claim 29 wherein said first and second inflow passageways have respective first and second inflow passageway lengths which are substantially equal, and wherein:
said first and second outflow passageways have respective first and second outflow passageway lengths which are substantially equal.

37. The apparatus of claim 36 wherein voltages of substantially equal magnitude and opposite polarity are respectively applied to said first and second electrode assemblies.

38. The apparatus of claim 37 further comprising an electrode at said entrance passageway which is coupled to an electrical ground.

39. The apparatus of claim 38 further comprising an electrode at said exit passageway which is coupled to an electrical ground.

40. The apparatus of claim 1 wherein said flowable material is liquid egg.

41. The apparatus of claim 40 wherein said liquid egg is heated from about 120° F. (about 49° C.) to about 280° F. (about 138° C.) as it passes from said entrance passageway to said exit passageway.

42. The apparatus of claim 41 wherein said liquid egg is heated from about 120° F. (about 49° C.) to about 150° F. (about 66° C.) as it passes from said entrance passageway to said first and second electrode assemblies.

43. The apparatus of claim 42 wherein said liquid egg is heated from about 150° F. (about 66° C.) to about 280° F. (about 138° C.) as it passes from said first and second electrode assemblies to said exit passageway.

44. The apparatus of claim 43 wherein said liquid egg passes through said outflow assembly at a predetermined flow rate so that said liquid egg is heated from about 150° F. (about 66° C.) to about 280° F. (about 138° C.) in a period of about 0.005 second.

45. The apparatus of claim 44 wherein said liquid egg is electroheated so as to produce shelf-stable liquid egg as it passes from said entrance passageway to said exit passageway.

46. The apparatus of claim 1 wherein said flowable material is milk.

47. The apparatus of claim 46 wherein said milk is electroheated so as to produce shelf-stable milk as it passes from said entrance passageway to said exit passageway.

48. The apparatus of claim 46 wherein said milk is heated from about 40° F. (about 4° C.) to about 280° F. (about 138° C.) as it passes from said entrance passageway to said exit passageway.

49. The apparatus of claim 48 wherein said milk is heated from about 40° F. (about 4° C.) to about 160° F. (about 71° C.) as it passes from said entrance passageway to said first and second electrode assemblies.

50. The apparatus of claim 49 wherein said milk is heated from about 160° F. (about 71° C.) to about 280° F. (about 138° C.) as it passes from said first and second electrode assemblies to said exit passageway.

51. The apparatus of claim 50 wherein said milk passes through said outflow assembly at a predetermined flow rate so that said milk is heated from about 160° F. (about 71° C.) to about 280° F. (about 138° C.) in a period of about 0.005 second.

52. A method of electroheating flowable material using apparatus, said apparatus comprising:
first and second electrode assemblies,
a dielectric inflow assembly having an entrance passageway and first and second inflow passageways which communicate with said entrance passageway, each of said inflow passageways having a diameter and a cross-sectional area, said first inflow passageway coupled to said first electrode assembly for allowing a first portion of said flowable material to flow from said entrance passageway to said first electrode assembly, said second inflow passageway coupled to said second electrode assembly for allowing a second portion of said flowable material to flow from said entrance passageway to said second electrode assembly, and
a dielectric outflow assembly having an exit passageway and fist and second outflow passageways which communicate with said exit passageway, each of said outflow passageways having a diameter and a cross-sectional area, said first outflow passageway coupled to said first electrode assembly, for allowing said first portion of said flowable material to flow from said first electrode assembly to said exit passageway, said second outflow passageway coupled to said second electrode assembly for allowing said second portion of said flowable material to flow from said second electrode assembly to said exit passageway, wherein:
each of said first and second electrode assemblies comprises at least one electrode which is in electrical contact with said flowable material, said at least one electrode having a surface area that is relatively large compared to said cross-sectional area of said inflow and outflow passageways so that the current density in the flowabLe material is relatively low near said at least one electrode, said flowable material having an electrical resistance inside every inflow passageway that is substantially equal, and wherein voltages of opposite polarity are respectively applied to said first and second electrode assemblies so that a first electric current passes through said first and second inflow passageways and a second electric current passes through said first and second outflow passageways, in order to electroheat said flowable material, said method comprising the steps of:
providing said flowable material;

conveying said first portion of said flowable material from said entrance passageway to said first electrode assembly;

conveying said second portion of said flowable material from said entrance passageway to said second electrode assembly;

conveying said first portion of said flowable material from said first electrode assembly to said exit passageway;

conveying said second portion of said flowable material from said second electrode assembly to said exit passageway;

applying said voltages of opposite polarity respectively to said first and second electrode assemblies so that said first current flows through said first and second portions of said flowable material as they are respectively conveyed from said entrance passageway to said first and second electrode assemblies, and so that said second current flows through said first and second portions of said flowable material as they are respectively conveyed from said first and second electrode assemblies to said exit passageway, in order to electroheat said first and second portions of said flowable material.

53. The method of claim 52 further comprising the step of:
cooling said flowable material after it has been conveyed to said exit passageway.

54. The method of claim 53 wherein said cooling step comprises the steps of:
conveying said flowable material through a first conduit to a mixing chamber;
conveying relatively cold flowable material to said mixing chamber so as to allow said flowable material and said relatively cold flowable material to mix together in order to form cooled flowable material;
conveying said cooled flowable material away from said mixing chamber.

55. The method of claim 54 wherein said cooling step further comprises suspending a ground electrode in said mixing chamber substantially adjacent said first conduit.

56. The method of claim 55 wherein said suspending step comprises suspending a ground electrode comprising graphite.

57. The method of claim 55 wherein said suspending step comprises suspending a ground electrode having a substantially circular cross section.

58. The method of claim 57 wherein said suspending step comprises suspending a disk-shaped ground electrode.

59. The method of claim 57 wherein said suspending step comprises:
suspending a hollow partial spherical ground electrode having a concave face; and
orienting said concave face toward said first conduit.

60. The method of claim 52 further comprising the step of providing an electrode at said entrance passageway which is coupled to an electrical ground.

61. The method of claim 52 further comprising the step of providing an electrode at said exit passageway which is coupled to an electrical ground.

62. The method of claim 52 wherein said applying step comprises applying voltages of substantially equal magnitude and opposite polarity respectively to said first and second electrode assemblies.

63. The method of claim 62 wherein said applying step comprises applying alternating voltages having a frequency up to about at least 100 kHz.

64. The method of claim 63 wherein said frequency is about 10 kHz.

65. The method of claim 63 wherein said frequency is between about 50 Hz and about 60 Hz.

66. The method of claim 52 wherein said flowable material is liquid egg.

67. The method of claim 66 wherein said liquid egg is electroheated from about 120° F. (about 49° C.) to about 280° F. (about 138° C.) as it is conveyed from said entrance passageway to said exit passageway.

68. The method of claim 67 wherein said liquid egg is heated from about 120° F. (about 49° C.) to about 150° F. (about 66° C.) as it is conveyed from said entrance passageway to said first and second electrode assemblies.

69. The method of claim 68 wherein said liquid egg is heated from about 150° F. (about 66° C.) to about 280° F. (about 138° C.) as it is conveyed from said first and second electrode assemblies to said exit passageway.

70. The method of claim 69 wherein said liquid egg is conveyed from said first and second electrode assemblies to said exit passageway at a predetermined flow rate so that said liquid egg is heated from about 150° F. (about 66° C.) to about 280° F. (about 138° C.) in a period of about 0.005 second.

71. The method of claim 66 wherein said liquid egg is electroheated so as to produce shelf-stable liquid egg as it is conveyed from said entrance passageway to said exit passageway.

72. The method of claim 52 wherein said flowable material is milk.

73. The method of claim 72 wherein said milk is electroheated so as to produce shelf-stable milk as it is conveyed from said entrance passageway to said exit passageway.

74. The method of claim 72 wherein said milk is heated from about 40° F. (about 4° C.) to about 280° F. (about 138° C.) as it is conveyed from said entrance passageway to said exit passageway.

75. The method of claim 74 wherein said milk is heated from about 40° F. (about 4° C.) to about 160° F. (about 71° C.) as it is conveyed from said entrance passageway to said first and second electrode assemblies.

76. The method of claim 75 wherein said milk is heated from about 160° F. (about 71° C.) to about 280° F. (about 138° C.) as it is conveyed from said first and second electrode assemblies to said exit passageway.

77. The method of claim 76 wherein said milk is conveyed from said first and second electrode assemblies to said exit passageway at a predetermined flow rate so that said milk is heated from about 160° F. (about 71° C.) to about 280° F. (about 138° C.) in a period of about 0.005 second.

78. Apparatus for electroheating a flowable material comprising:
a first conduit having a diameter and a cross-sectional area through which said flowable material flows from a first end to a second end;
a first electrode assembly in electrically conductive relationship with said first conduit for providing a first supply voltage to said flowable material at a location along said first conduit;
a receiving chamber at said second end of said first conduit having a first inlet into which said flowable material flows from said first conduit; and
an outlet ground electrode suspended in said receiving chamber adjacent said first chamber inlet;
a second conduit having a diameter and a cross-sectional area through which said flowable material flows, said first and second conduits having a common conduit inlet and a common conduit outlet, said receiving chamber being adjacent said common conduit outlet; and a second electrode assembly in electronically conductive relationship with said second conduit for providing a second supply voltage to said flowable material at a location along said second conduit, wherein said first supply voltage and said second supply voltage are of opposite polarity, each of said first and second electrode assemblies comprises at least one, electrode which is in electrical contact with said flowable material, said at least one electrode having a surface area that is relatively large compared to said cross-sectional areas of said conduits so that the current density in the flowable material is relatively low near said at least one electrode, said flowable material having an electrical resistance inside said circuit that is substantially equal; whereby:

(1) current flows from said first supply electrode through said flowable material to said outlet ground electrode, thereby heating said flowable material in said first conduit, and (2) current flows also from said second supply electrode through said flowable material to said outlet ground electrode, thereby beating said flowable material in said second conduit.

79. The apparatus of claim 78 wherein said receiving chamber has a second inlet for allowing relatively cold flowable material to enter said mixing chamber and mix with said flowable material in order to form cooled flowable material; and an outlet for allowing said cooled flowable material to exit said mixing chamber.

80. The apparatus of claim 79 further comprising an expansion chamber upstream of said first inlet for increasing holding time of said heated flowable material before cooling in said receiving chamber.

81. The apparatus of claim 78 wherein said outlet ground electrode comprises graphite.

82. The apparatus of claim 78 wherein said outlet ground electrode has a substantially circular cross section.

83. The apparatus of claim 82 wherein said outlet ground electrode is a disk.

84. The apparatus of claim 82 wherein said outlet ground electrode is a hollow partial sphere having a concave face facing said first chamber inlet.

85. The apparatus of claim 78 wherein said first and second supply electrodes are connected to a single electrical supply.

86. The apparatus of claim 78 wherein said first and second supply electrodes are connected to a floating power supply.

87. The apparatus of claim 78 further comprising an inlet ground electrode suspended in said flowable material adjacent said common conduit inlet.

88. The apparatus of claim 87 wherein said inlet ground electrode comprises graphite.

89. The apparatus of claim 87 wherein said inlet ground electrode has a substantially circular cross section.

90. The apparatus of claim 89 wherein said inlet ground electrode is a disk.

91. The apparatus of claim 89 wherein said inlet ground electrode is a hollow partial sphere having a concave face facing in a direction toward said supply electrodes.

92. The apparatus of claim 78 further comprising an inlet ground electrode suspended in said flowable material adjacent said first end of said first conduit.

93. The apparatus of claim 92 wherein said inlet ground electrode comprises graphite.

94. The apparatus of claim 92 wherein said inlet ground electrode has a substantially circular cross section.

95. The apparatus of claim 94 wherein said inlet ground electrode is a disk.

96. The apparatus of claim 94 wherein said inlet ground electrode is a hollow partial sphere having a concave face facing in a direction toward said first supply electrode.

97. Apparatus for electroheating a flowable material comprising:

a first conduit having a diameter and cross-sectional area through which said flowable material flows, said first conduit having a diameter and a cross-sectional area;

a first electrode assembly in electrically conductive relationship with said conduit for providing a first supply voltage to said flowable material at a location along said conduit;

a receiving chamber into which said flowable material flows from said first conduit, said conduit extending into said receiving chamber and having an aperture therein adjacent an end thereof; and a ground electrode fixed to said conduit at said end and adjacent said aperture, said flowable material flowing into said receiving chamber through said aperture;

a second conduit having a diameter and a cross-sectional area through which said flowable material flows, said first and second conduits having a common conduit inlet and a common conduit outlet, said receiving chamber being adjacent said common conduit outlet; and a second electrode assembly in electronically conductive relationship with said second conduit for providing a second supply voltage to said flowable material at a location along said second conduit, wherein said first supply voltage and said second supply voltage are of opposite polarity, each of said first and second electrode assemblies comprises at least one electrode which is in electrical contact with said flowable material, said at least one electrode having a surface area that is relatively large compared to said cross-sectional areas of said conduits so that the current density in the flowable material is relatively low near said at least one electrode, said flowable material having an electrical resistance inside said conduits that is substantially equal; whereby:

(1) current flows from said first supply electrode through said flowable material to said ground electrode, thereby heating said flowable material, and (2) current flows also from said second supply electrode through said flowable material to said ground electrode, thereby heating said flowable material in said second conduit.

98. The apparatus of claim 97 wherein said receiving chamber has an inlet for allowing relatively cold flowable material to enter said mixing chamber and mix with said flowable material in order to form cooled flowable material; and an outlet for allowing said cooled flowable material to exit said mixing chamber.

99. The apparatus of claim 98 further comprising an expansion chamber upstream of said aperture for increasing holding time of said heated flowable material before cooling in said receiving chamber.

100. The apparatus of claim 97 wherein said ground electrode comprises graphite.

101. The apparatus of claim 97 wherein said ground electrode has a substantially circular cross section.

102. The apparatus of claim 101 wherein said ground electrode is a disk.

103. The apparatus of claim 101 wherein said ground electrode is a hollow partial sphere having a concave face facing into said conduit.

* * * * *